United States Patent [19]

Brennan et al.

[11] 4,149,988

[45] Apr. 17, 1979

[54] DECOMPOSITION INHIBITORS FOR CHLOROISOCYANURATES

[75] Inventors: James P. Brennan, Wallingford; John M. Casberg, Cheshire; Clair H. Putnam, Madison, all of Conn.

[73] Assignee: Olin Corporation, New Haven, Conn.

[21] Appl. No.: 800,828

[22] Filed: May 26, 1977

[51] Int. Cl.$^2$ .......................... C11D 3/48; C11D 3/24; C11D 3/395
[52] U.S. Cl. .................................... 252/187 C; 8/109; 252/94; 252/95; 252/99; 544/190
[58] Field of Search ................. 252/187 C, 94, 95, 99; 8/109; 260/248 C

[56] References Cited

U.S. PATENT DOCUMENTS

| | | | |
|---|---|---|---|
| 3,431,206 | 3/1969 | Hilton et al. | 252/187 C |
| 3,454,699 | 7/1969 | Symes | 252/187 C |

*Primary Examiner*—Benjamin R. Padgett
*Assistant Examiner*—Irwin Gluck
*Attorney, Agent, or Firm*—James B. Haglind; Donald F. Clements

[57] ABSTRACT

Decomposition of chloroisocyanurates such as trichloroisocyanuric acid or alkali metal dichloroisocyanurates is inhibited by the presence of alkaline earth metal sulfates. The sulfates may be used in compositions with a solid chloroisocyanurate or they may be added separately, for example, to packages containing the chloroisocyanurate.

23 Claims, No Drawings

DECOMPOSITION INHIBITORS FOR CHLOROISOCYANURATES

This invention relates to improved packaging for chloroisocyanurate compositions used as dry sanitizing and disinfecting agents.

Chloroisocyanurates such as trichloroisocyanuric acid have a degree of instability which, for example, in the presence of moisture or heat results in their decomposition. This decomposition includes the evolution of highly noxious and otherwise objectionable chloramine gases such as nitrogen trichloride. U.S. Pat. No. 3,183,057 issued to H. C. Marks, R. R. Joiner and G. U. Glasgow teach the generation of these gases from dry solid N-chloro compounds by their reaction with acidic and alkaline reagents in the presence of moisture. The reagents are enclosed in a moisture permeable envelope which allows sufficient moisture to initiate and sustain the reaction to evolve the chloramine gases. Water soluble acids and alkaline reagents are employed as reactants together with dichloroisocyanuric acid or trichloroisocyanuric acid. The envelope may contain as simple carriers or diluents inert substances such as calcium sulfate, or magnesium sulfate.

It is frequently desirable, however, to produce packages for chloroisocyanurates in which the evolution of the pungent, nauseating chloramine gases is inhibited by a deodorizing agent.

U.S. Pat. No. 2,897,154, issued to R. L. Low teaches the use of silver compounds such as silver nitrate, silver phosphate, silver oxide, or silver carbonates, as well as mercuric nitrate. These salts are expensive to employ, and in addition, the use of mercuric nitrate may impose a pollution problem.

Materials such as mixtures of manganese dioxide and cupric oxide, activated alumina, activated carbon, zeolites, bentonite, alkali metal silicates, alkali metal hydroxides, potassium, rubidium or cesium carbonates, or alkaline earth oxides are described as suitable deodorants in U.S. Pat. No. 3,061,549, issued to M. L. Dickey. Included among these materials are those which are potentially reactive with chloroisocyanurates such as the hydroxides and carbonates as well as those which are moisture sensitive, for example, alkali metal silicates and carbonates and alkaline earth metal oxides.

Sulfur-containing reducing agents such as alkali metal sulfides, alkali metal sulfites or alkali metal dithionites are described as stabilizing agents for chloroisocyanuric acids in German Pat. No. 1,111,198, issued to R. Merkel, A. Palm and H. Werner. These materials, however, permit the accumulation of excessive moisture when used in a warm, moist atmosphere.

Surprisingly, it has now been found that compounds believed to be inert ingredients in compositions used to evolve chloramines have now been found to effectively inhibit that evolution.

It is an object of the present invention to provide decomposition inhibitors which are effective in preventing the accumulation of noxious gases in packages containing chloroisocyanurates.

An additional object of the present invention is to provide decomposition inhibitors which are insensitive to moisture and non-reactive with chloroisocyanurates.

Another object of the invention is to provide decomposition inhibitors which are aesthetically pleasing in a chloroisocyanurate package.

A further object of the present invention is to provide decomposition inhibitors which are inexpensive to use.

These and other objects of the present invention are accomplished by a composition consisting essentially of a solid chloroisocyanurate and a decomposition inhibiting portion of an alkaline earth metal sulfate.

This novel decomposition inhibitor is preferably used in a moisture resistant package containing the chloroisocyanurate.

Dry solid chloroisocyanurates which can be enclosed in the novel packages of the present invention include, for example, trichloroisocyanuric acid, dichloroisocyanuric acid and alkali metal salts of dichloroisocyanuric acid such as sodium dichloroisocyanurate. As previously stated, these compounds are sensitive to moisture or heat which may result in some decomposition to produce chloramine gases such as nitrogen trichloride.

Effective in inhibiting the evolution of odorous chloramine gases are alkaline earth metal sulfates such as calcium sulfate, magnesium sulfate or mixtures thereof. Any suitable amount of alkaline earth metal sulfate may be used which will effectively inhibit the evolution and accumulation of chloramine gases. Suitable amounts include from about 0.01 to about 20 percent by weight of the chloroisocyanurate.

Present as dry solids, the alkaline earth metal sulfates may be combined with the solid chloroisocyanurate, for example, in a granular composition such as a tablet or briquette. The two solid components may also be present in a simple physical mixture. Further, where the chloroisocyanurate is itself in the product form of a tablet or briquette, the presence of alkaline earth sulfate as a separate granular solid provides effective inhibition to decomposition and prevents the evolution and accumulation of offensive chloramine gases. When employed in granular compositions or mixtures preferred amounts of alkaline earth metal sulfate are those from about 0.1 to about 15, and more preferably from about 1 to about 5 percent by weight of the chloroisocyanurate.

In a further embodiment, the chloroisocyanurate as a tablet or briquette is housed in a container where the entire container is enclosed by the moisture resistant package. The alkaline earth metal sulfate, though physically separated from the chloroisocyanurate, effectively inhibits the evolution of chloramine gases from the chloroisocyanurate. When used, for example, in packaging applications preferred amounts of alkaline earth metal sulfate are those from about 0.01 to about 10, more preferably from about 0.1 to about 1 percent by weight of the chloroisocyanurate.

Where the decomposition inhibitor is physically separated from the chloroisocyanurate, it may be advantageous to admix with alkaline earth metal sulfate other agents which aid in inhibiting decomposition of chloroisocyanurates. For example, mixtures of alkaline earth metal sulfates and alkali metal bicarbonates are quite suitable for inhibiting decomposition of chloroisocyanurates when included in moisture resistant packages. The alkali metal bicarbonate is present in an amount, for example, of from about 10 to about 90, preferably from about 30 to about 70 percent by weight of the alkaline earth metal sulfate. While any of the alkali metal bicarbonates may be employed, sodium bicarbonate is a preferred embodiment.

Additionally, mixtures of alkali metal sulfites, such as sodium sulfite, with alkaline earth metal sulfates are suitable decomposition inhibitors. Suitable amounts of alkali metal sulfites which are used include amounts of from about 10 to about 90, preferably from about 30 to about 70 percent by weight of the alkaline earth metal sulfate.

Moisture resistant packaging materials are employed to minimize the possibility of decomposing the chloroisocyanurate by moisture. Suitable packaging materials include glass or plastic materials such as polyethylene, polypropylene, polyvinyl chloride and polyvinylidene chloride.

The novel compositions of the present invention are further illustrated by the following examples. All percentages are by weight unless otherwise specified.

EXAMPLE 1

Calcium sulfate (2 grams) was admixed with 98 grams of trichloroisocyanuric acid and the mixture placed in a septum vial. The vial was sealed, wrapped in tin foil, and placed in a closed carton at ambient temperature. After 30 days, a 1 ml. sample of gas was removed from the vial and the gas analyzed in a gas chromatograph. Nitrogen trichloride in a concentration of less than 0.05 percent was detected.

Comparative Test

Trichloroisocyanuric acid, 100 grams, was placed in a septum vial and the procedure of the Example duplicated. The gas sample had a nitrogen trichloride of greater than 1 percent.

The addition of calcium sulfate to the trichloroisocyanuric acid so inhibited decomposition that less than 1/20th of the amount of nitrogen trichloride was evolved as compared to the amount produced by trichloroisocyanuric acid in the absence of calcium sulfate.

EXAMPLE 2

A cartridge containing tablets of trichloroisocyanuric acid was put into a polyethylene bag having a single wall 3 mls. thick. Also introduced into the bag was 3 grams of calcium sulfate. The bag was heat sealed and stored in a control room having a temperature of 100° F. and a relative humidity of 98 percent. After 2 months, the bag was examined and found to have no moisture condensation present inside the bag.

Comparative Test

The procedure of Example 2 was duplicated exactly with the exception that the polyethylene bag contained 3 grams of sodium sulfite. After 2 months in the control room, polyethylene bag contained visible beads of moisture.

EXAMPLE 3

The procedure of Example 2 was employed with the substitution of a mixture of 1.5 grams of calcium sulfate and 1.5 grams of sodium bicarbonate being used in place of the calcium sulfate alone. After storage in the control room for 2 months, an examination of bag showed no signs of moisture condensation.

EXAMPLE 4

A container filled with about 120 tablets of trichloroisocyanuric acid was inserted in a double layer polyethylene bag having a thickness of about 6 mils. The container included a label having a portion which was orange in color and plastic inserts which were colored red. A mixture of 1.5 grams of $CaSO_4$ and 1.5 grams of $Na_2SO_3$ was added to the bag as a decomposition inhibitor. The bag was then heat sealed and stored in a control room at a temperature of 100° F. and a relative humidity of 98 percent. After 1 month, the bag and the container were examined. No evidence was found of discoloration of the container's label nor of the plastic inserts.

Comparative Test

The procedure of Example 4 was repeated using an identical container filled with identical trichloroisocyanuric acid with the exception that no decomposition inhibitor was added to the bag prior to heat sealing. Examination of the bag and the container following one month storage in the same control room under the same conditions showed that both the label and the plastic inserts of the container had slightly been bleached.

EXAMPLE 5

The procedure of Example 1 was duplicated exactly with the exception that 2.0 grams of magnesium sulfate were substituted for calcium sulfate. After 60 days a 1 ml. sample of gas was removed and analyzed in a gas chromatograph. Nitrogen trichloride in a concentration of about 0.01 percent was detected.

EXAMPLE 6

The procedure of Example 5 was duplicated exactly with the exception that sodium dichloroisocyanurate dihydrate (98.0 grams) was substituted for trichloroisocyanuric acid. After 60 days analysis of the gas sample found $NCl_3$ in a concentration of less than 0.01 percent.

EXAMPLE 7

The procedure of Example 6 was duplicated exactly with the substitution of calcium sulfate (2.0 grams) for magnesium sulfate. Analysis of the gas sample from the mixture with sodium dichloroisocyanurate dihydrate showed a concentration of $NCl_3$ of about 0.01 percent after storage for 60 days.

EXAMPLE 8

Tablets were prepared from a mixture of 98.65 percent trichloroisocyanuric acid, 1 percent $MgSO_4$, 0.1 percent sodium stearate and 0.25 percent blue dye, where all percents are those by weight. A container was filled with the tablets and the container placed in a moisture resistant single walled polyethylene bag. The container enclosed red colored plastic inserts and a label having a portion colored orange. The bag was stored in a control room at a temperature of 100° F., at a relative humidity of 90 percent for a period of 23 days. Examination of the container showed that no bleaching of the colored portion of the label or the plastic inserts had taken place.

What is claimed is:

1. A composition consisting of a solid chloroisocyanurate selected from the group consisting of trichloroisocyanuric acid, dichloroisocyanuric acid and alkali metal salts of dichloroisocyanuric acid and a decomposition inhibiting portion of an alkaline earth metal sulfate.

2. The composition of claim 1 in which said decomposition inhibiting portion is from about 0.01 to about 20 percent by weight of said solid chloroisocyanurate.

3. The composition of claim 2 in which said alkaline earth metal sulfate is selected from the group consisting of calcium sulfate and magnesium sulfate.

4. The composition of claim 3 in which said chloroisocyanurate is trichloroisocyanuric acid or sodium dichloroisocyanurate.

5. The composition of claim 4 in which said alkaline earth metal sulfate is anhydrous.

6. The composition of claim 5 in which said decomposition inhibiting portion is from about 0.1 to about 15 percent by weight of said solid chloroisocyanurate.

7. The composition of claim 5 in which said alkaline earth metal sulfate is calcium sulfate.

8. The composition of claim 5 in which said alkaline earth metal sulfate is magnesium sulfate.

9. A moisture resistant package containing a solid chloroisocyanurate capable of evolving a gaseous chloramine compound on decomposition and a decomposition inhibitor selected from the group consisting of an alkaline earth metal sulfate and mixtures of said alkaline earth metal sulfate with an alkali metal bicarbonate or an alkali metal sulfite, which is capable of inhibiting the evolution of said gaseous chloramine compound, said solid chloroisocyanurate being selected from the group consisting of trichloroisocyanuric acid, dichloroisocyanuric acid and alkali metal salts of dichloroisocyanuric acid.

10. The moisture resistant package of claim 9 in which said decomposition inhibitor is present in an amount from about 0.01 to about 10 percent by weight of said chloroisocyanurate.

11. The moisture resistant package of claim 10 in which said decomposition inhibitor is selected from the group consisting of calcium sulfate and magnesium sulfate.

12. The moisture resistant package of claim 11 in which said chloroisocyanurate is trichloroisocyanuric acid or sodium dichloroisocyanurate.

13. The moisture resistant package of claim 12 in which said decomposition inhibitor is calcium sulfate present in an amount of from about 0.1 to about 1 percent by weight of said chloroisocyanurate.

14. The moisture resistant package of claim 10 in which said decomposition inhibitor is physically separate from said chloroisocyanurate.

15. The moisture resistant package of claim 9 in which said decomposition inhibitor is a mixture of said alkaline earth metal sulfate and an alkali metal bicarbonate.

16. The moisture resistant package of claim 15 in which said alkali metal bicarbonate is present in an amount of from about 10 to about 90 percent by weight of said alkaline earth metal sulfate.

17. The moisture resistant package of claim 16 in which said chloroisocyanurate is trichloroisocyanuric acid and said alkaline earth metal sulfate is calcium sulfate or magnesium sulfate.

18. The moisture resistant package of claim 17 in which said alkaline earth metal sulfate is calcium sulfate and said alkali metal bicarbonate is sodium bicarbonate.

19. The moisture resistant package of claim 14 in which said decomposition inhibitor is a mixture of said alkaline earth metal sulfate and an alkali metal sulfite.

20. The moisture resistant package of claim 19 in which said alkali metal sulfite is present in an amount of from about 10 to about 90 percent by weight of said alkaline earth metal sulfate.

21. The moisture resistant package of claim 20 in which said alkaline earth metal sulfate is calcium sulfate or magnesium sulfate.

22. The moisture resistant package of claim 21 in which said composition is sodium sulfite.

23. The moisture resistant package of claim 11 in which said alkaline earth metal sulfate is magnesium sulfate.

* * * * *